US008623912B2

(12) United States Patent
Tang et al.

(10) Patent No.: US 8,623,912 B2
(45) Date of Patent: Jan. 7, 2014

(54) FOSTRIECIN DERIVATIVES AND THE PHARMACEUTICAL USES THEREOF

(75) Inventors: Li Tang, Beijing (CN); Rongguo Qiu, Beijing (CN)

(73) Assignees: Beijing Biostar Technologies, Ltd., Beijing (CN); Dalian University of Technology, Liaoning (CN)

( * ) Notice: Subject to any disclaimer, the term of this patent is extended or adjusted under 35 U.S.C. 154(b) by 438 days.

(21) Appl. No.: 12/896,144

(22) Filed: Oct. 1, 2010

(65) Prior Publication Data

US 2012/0065171 A1     Mar. 15, 2012

Related U.S. Application Data

(63) Continuation of application No. PCT/CN2009/000366, filed on Apr. 3, 2009.

(30) Foreign Application Priority Data

Apr. 3, 2008   (CN) .......................... 2008 1 0091830

(51) Int. Cl.
*A61K 31/351*      (2006.01)
*C07D 309/16*      (2006.01)

(52) U.S. Cl.
USPC ........... 514/460; 549/263; 549/273; 549/293; 514/449; 514/451

(58) Field of Classification Search
USPC ................. 549/200, 218, 222, 263, 273, 293; 514/449, 451, 460
See application file for complete search history.

(56) References Cited

U.S. PATENT DOCUMENTS

| 4,578,383 | A | 3/1986 | Stampwala et al. | |
|---|---|---|---|---|
| 5,036,008 | A | 7/1991 | Ohkuma et al. | |
| 7,650,848 | B2 * | 1/2010 | Brennan et al. | 114/222 |
| 8,263,125 | B2 * | 9/2012 | Vaya et al. | 424/469 |

FOREIGN PATENT DOCUMENTS

| EP | 0087021 A2 | 8/1983 |
|---|---|---|
| EP | 0128651 A2 | 12/1984 |

OTHER PUBLICATIONS

Hokanson, G.C., et al, "Novel antitumor agents CI-920, PD 113270, and PD 113271", *Journal of Organic Chemistry*, 1985, vol. 50. No. 4, pp. 462-466.
Takeuchi, T., et al, Total Synthesis and Stereochemistry of the Antitumor Antibiotic PD 113271:, *Organic Letters*, 2006, vol. 8, No. 23, pp. 5307-5310.
Maki, K., et al, "Catalyst-Controlled Asymmetric Synthesis of Fostriecin and 8-epi-Fostriecin", *Journal of the American Chemical Society*, 2005, vol. 127, No. 48, pp. 17111-17117.
Buck, S.B., et al, "Fundamental Role of the Fostriecin Unsaturated Lactone and Implications for Selective Protein Phosphatase Inhibition", *Journal of the American Chemical Society*, 2003, vol. 125, No. 51, pp. 15694-15695.
Ohkuma, H., et al., "Sultriecin, a new antifungal and antitumor antibiotic from Streptomyces roseiscleroticus: production, isolation, structure and biological activity", *Journal of Antibiotics*, 1992, vol. 45, No. 8, 1239-49.
International Search Report for International Application No. PCT/CN2009/000366 issued by the Chinese Patent Office, mailed on Jul. 2, 2009.
Lewy et al., "Fostriecin: Chemistry and Biology", *Current Medicinal Chemistry*, 2002, No. 9, pp. 2005-2032.

* cited by examiner

*Primary Examiner* — Golam M M Shameem
(74) *Attorney, Agent, or Firm* — RatnerPrestia

(57) ABSTRACT

Novel Fostriecin (or FST) derivatives represented by formula (I), the pharmaceutical compositions and preparation methods thereof. The pharmaceutical uses of these compounds, especially the use for the preparation of pharmaceutical compositions for treating tumor, inhibiting cell over growth, or lowering myocardial infarction and the injury to cells.

formula I

8 Claims, 2 Drawing Sheets

FOSTRIECIN DERIVATIVES AND THE PHARMACEUTICAL USES THEREOF

This application is a continuation application of International Application No. PCT/CN2009/000366, filed Apr. 3, 2009, which claims priority to Chinese Application No. 200810091830.4, filed Apr. 3, 2008.

FIELD OF THE INVENTION

The present invention relates to a series of novel Fostriecin derivatives, especially relates to series of thiophosphate, and other phosphate analogous or phosphate mimic of Fostriecin derivatives (FST derivatives), and also relates to a method for preparing the compound, a pharmaceutical composition comprising the compound and pharmaceutical uses thereof.

BACKGROUND OF THE INVENTION

Fostriecin (or FST) is a polyketide with phosphate compound inititally separated (1983) from soil bacteria, *Streptomyces pulveraceus*. Fostriecin was also successfully synthesized via total synthesis by the research group of Boger in 2001. Meanwhile, other compounds (PD113270 and PD113271) with similar structure were also separated and detected in the natural FST producing strains having the structural formula below (see Lewy et. al., 2002).

The in vitro activity of FST on tumor cells such as leukaemia, lung cancer, breast cancer

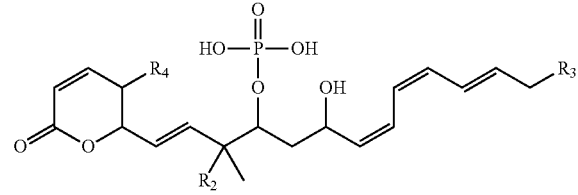

Fostriecin: $R_4$ = H, $R_2$ = $R_3$ = OH
PD113270: $R_4$ = $R_3$ = H, $R_2$ = OH
PD113271: $R_4$ = $R_3$ = $R_2$ = OH and ovarian cancer is well-known in the art (leukaemia cells L1210, $IC_{50}$=0.46 mM), FST is also effective in anti-tumors in vivo. Generally speaking, the activitiy of FST in anti-tumor is due to the selective inhibition on protein phophatase PP2A ($IC_{50}$=1.5 nM) and PP4 ($IC_{50}$=3 nM). It has been reported that the chemical synthetic and the naturally occurring FST analogues possess similar activities. For details of FST and analogues thereof, by reference, see Lewy et. al., 2002, "Fostriecin: Chemistry and Biology" Current Medicinal Chemistry 9: 2005-2032. Phase I of the clinical test for FST was stopped due to the difficulty in controlling the chemical purity of the products among different batches and the relatively low stability of the compounds both in vitro and in vivo (e.g. the dephosphation of FST results in the inactivated dephosphorylated FST). Development of FST derivatives of high purity, especially of high stability is highly required.

FST is a weak inhibitor against topoisomerase II ($IC_{50}$=50 mM), which, however, is the most powerful selective PP2A and PP4 inhibitor. Since some other protein phophatase inhibitors such as okadaic acid and calyculin A generally exhibit the tumor-promoting activity rather than the anti-tumor activity, people are interested in the correlation of the anti-tumor activity of FST with its enzymatic inhibitory activity. In addition, it should be noted that FST can promote the compaction of chromatin, and render the tumor cells sensitive to radiotherapy. Therefore, in order to obtain an effective therapeutic approach in treating tumors or other diseases, development of a series of novel FST analogues either for single administration or combinatory administration is highly required. If it is possible to prepare some FST derivatives with higher stability, such kind of compounds must be clinically more effective, and hence, become a more effective means for treating cancers and are promising to become a novel anti-tumor drug having a novel mechansium of action.

SUMMARY OF THE INVENTION

The objective of the present invention is to provide a series of novel and more stable FST compounds, and to provide the methods for preparing the same, for example by means of chemical modifications and/or genetic engeneering method. The present invention also provides a pharmaceutical composition comprising said compound, and use of said FST compounds in the preparation of the pharmaceutical composition for antitumor, inhibition of cell excessive growth, termination of cell growth, or reduction of myocardial infarction and injury to a cell.

The present invention provides a FST derivative of the following formula (I),

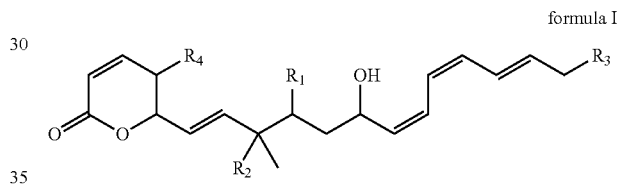

formula I wherein,
R1 is

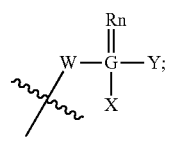

R1 is not a phosphate group;
R2, R3, R4 are each independently selected from H, OH, OR5, NHR$_6$ and a lower alkyl group;
W is O, O-CRjRj or NRj;
G is P, S or C;
X is SR$_6$, OR$_5$ or NHRj, as G is S, X=NRj or =O;
Y is OR$_5$, NHRj, CF$_3$, an unsubstituted lower alkyl group or a lower alkyl group substituted by a hydroxyl group, a lower acyloxy group, a lower alkanoyl group, a lower alkoxyl group, an amino group, a halogen, a lower alkylamido group or a lower amido group;
R$_5$ and R$_6$ are each H, Na, K, or an unsubstituted lower alkyl group or a lower alkyl group substituted by a hydroxyl group, a lower acyloxy group, a lower alkanoyl group, a lower alkoxyl group, an amino group, a halogen, a lower alkylamido group or a lower amido group;
As G is C, X does not exist;
Rj is H, OH, an alkyl group or a halogen, wherein said halogen is preferably fluorine (F).
Rn is O, NRj or S.

The term "lower" refers to the number of carbon atoms of 1 to 4.

The Compound of formula I can be obtained by subjecting FST or the derivative thereof, for example, PD113270 as described above, to biological and/or chemical modifications for dephosphorylation, followed by modifications of the phosphate derivative.

The compound of the present invention comprises the FST derivative of formula (II), which is a thiophosphorylated FST, see the following formula (II).

formula II

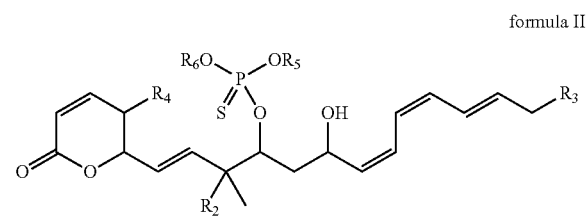

Firstly, dephosphorylated FST can be obtained by biochemical enzymolysis (as described in Example 1) or fermentation of a recombinant genetic engineering strain (as described in Example 2). Said recombinant genetic engineering strain comprises a modified-FST biosynthetic enzyme gene in which the DNA sequence (fosK gene) for encoding phosphorylated kinases (homoserine kinases) is inactivated by mutation, deletion or substitution of recombinant techniques. Said phosphorylated enzyme (kinases) FosK is responsible for the FST phosphorylation in FST biosynthesis.

Dehydroxylated FST can be obtained by fermentation of a recombinant genetic engineering strain of the present invention. Said strain comprises a modified FST biosynthetic enzyme gene in which the DNA sequence for encoding one of the three cytochrome P450 hydroxylated enzymes in a FST biosynthetic enzyme gene in a FST producing strain is inactivated by mutation, deletion or substitution of recombinant techniques. FST biosynthetic enzyme comprises three P450 gene encoding hydroxylated enzymes responsible for the hydroxylation to be taken place at C8 and C18 for FST, and at C4 for PD 113, 271, respectively.

The genetic engineering strain of the present invention is obtained by DNA recombinant technique, by which a recombinant genetic engineering producing strain is obtained as a result of inactivation or substitution of one or more genes or functional groups involved in the FST biosynthesis by means of homologous recombination, i.e., cloning a gene or the functional group need to be modified to a suicide vector, followed by double-crossover between the gene in the suicide vector with the homologous gene of the genome contained in nucleus of the host cell. Said inactivation can be achieved by random or point genetic mutation, deletion or substitution. Thus obtained recombinant biosynthetic gene is different from the natural biosynthetic gene, and FST derivatives can be produced in the recombinant host cell as the main product.

Compounds of formula I in some embodiments according to the present invention can be prepared from dephosphorylated FST or derivatives thereof using the general method as shown in the reaction scheme 1 below. The particularly preferable compound A can also be prepared from dephosphorylated FST using the method as described in Example 3 or the general method as shown in the reaction scheme 1.

Reaction scheme 1:

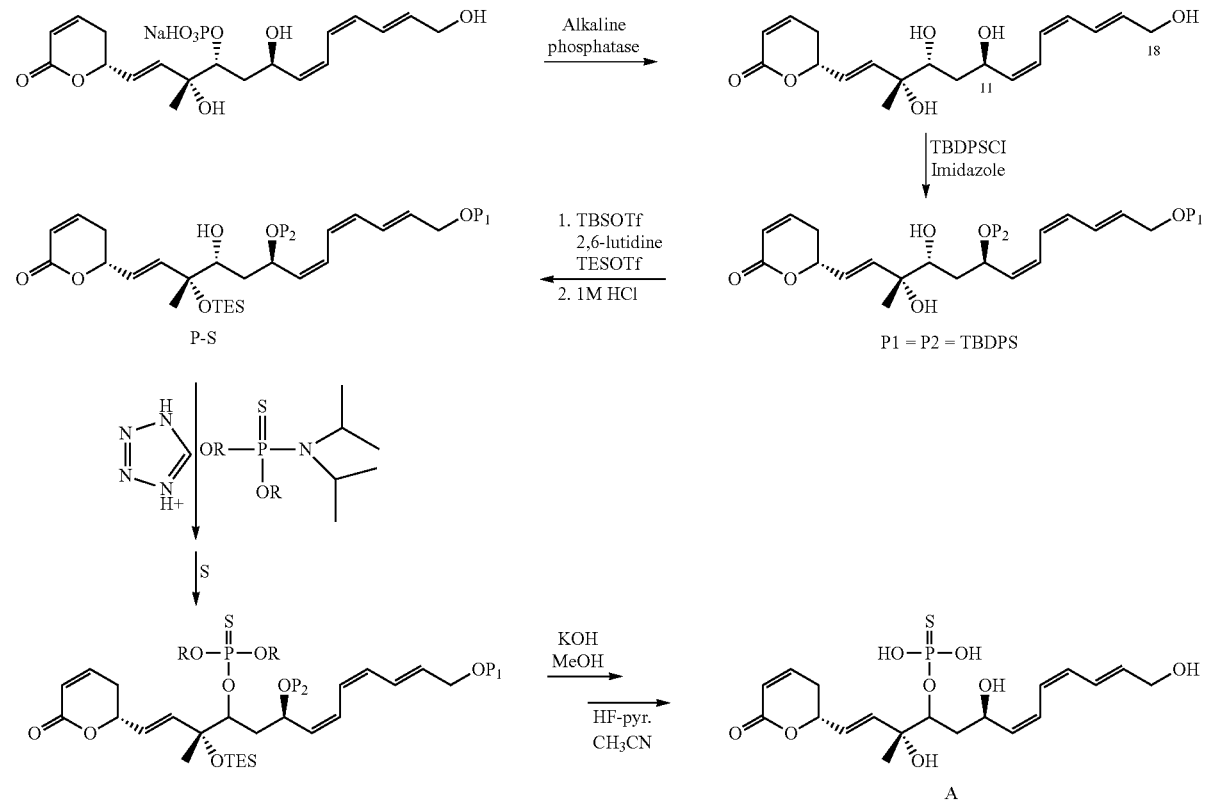

1. FST is subjected to biochemical enzymolysis to afford the dephosphorylated FST.

2. Protecting groups may be present in the FST compounds to protect the corresponding functional groups from undergoing any undesirable side reactions, such as acylation, etherification, oxidation, solvolysis and the like. The protecting groups are characterized in that they get easily to be removed by solvolysis, reduction, and photolysis or by enzyme, and that they do not exist in the end products. For example, firstly the free 11-hydroxyl group and 18-hydroxyl group of FST are protected by TBDPS protecting groups, and then the free 8-hydroxyl group of FST is selectively protected by TES or TBS protecting group, to afford the protected dephosphorylated FST intermediate (P—S).

3. The protected dephosphorylated FST intermediate (P—S) is reacted with bis-(2-cyanoethyl)-N,N-diisopropylphosphoramidite and tetrazole, and to which is then added with sulphur, to afford the protected thiophosphorylated FST intermediate.

4. The bis-2-cyanoethyl protecting groups of the thiophosphate moiety in the protected thiophosphorylated FST intermediate are removed by reacting with postassium hydroxide in methanol, and then the hydroxyl-protecting group in the thiophosphorylated FST intermediate is deprotected by common methods known in the art, for example, by treating with HF-pyridine in HF—MeCN to afford the thiophosphorylated FST derivative A.

Compounds of formula I in some embodiments according to the present invention can be prepared from dephosphorylated FST or derivatives thereof using the general method as shown in the reaction scheme 2 below, for example, the particularly preferable compounds B, C and D. The particularly preferable compound B can be prepared from dephosphorylated FST using the method as described in Example 4.

Reaction scheme 2:
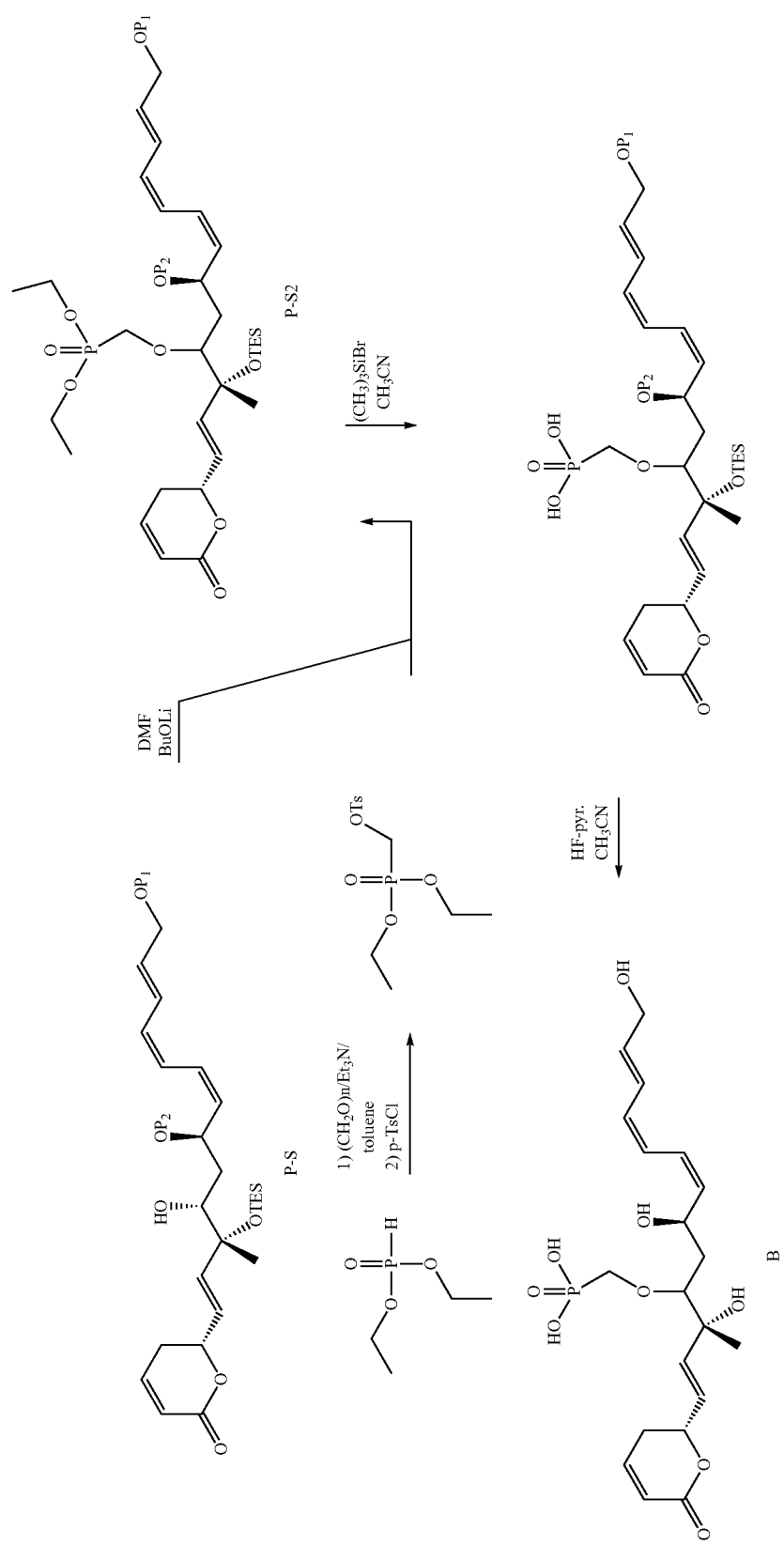

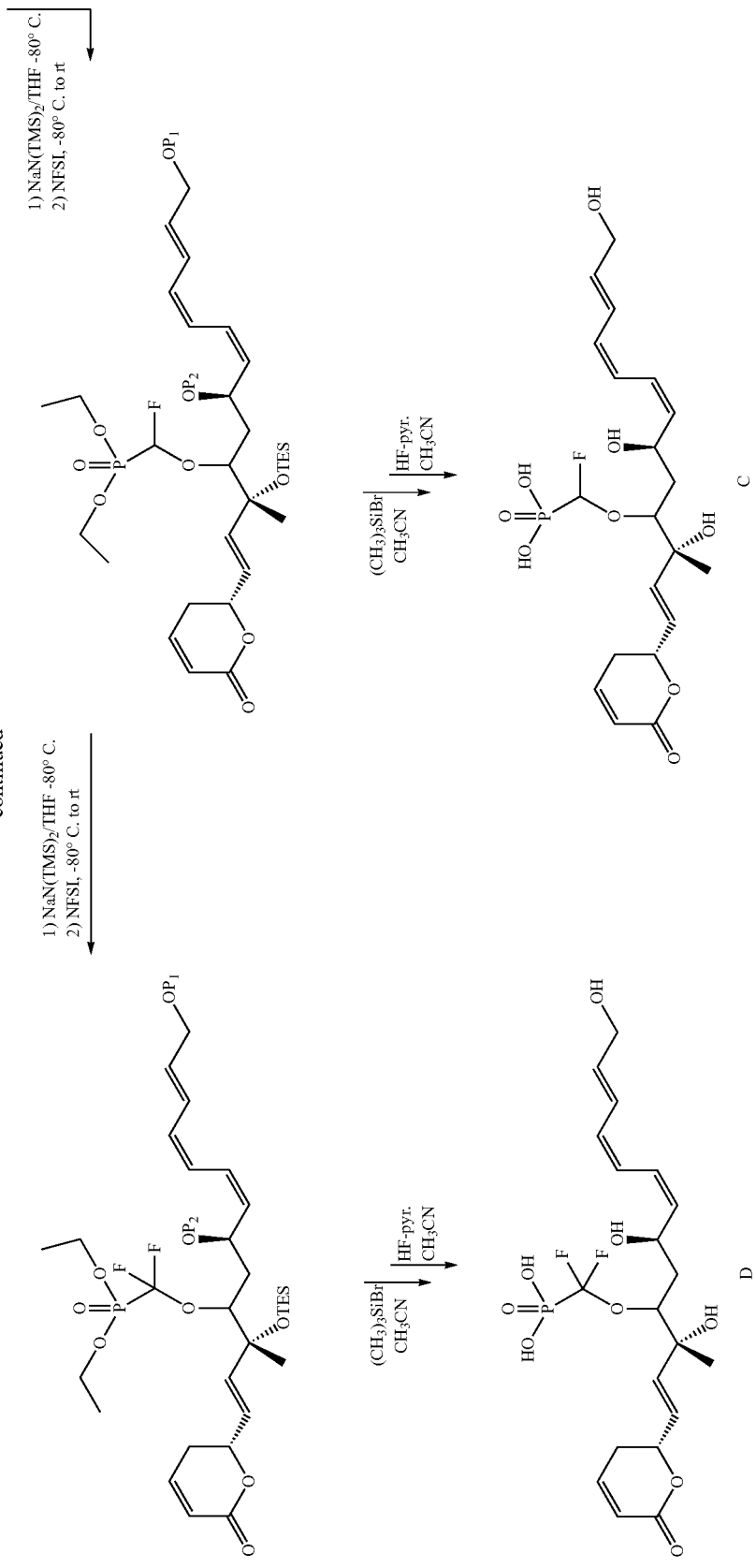

1. In toluene, a mixture of diethyl phosphate, polyoxymethylene and triethylamine is heated to 87° C. and reacted for 2 hours to afford the Ps-3 compound.

2. A 2M solution of lithium tert-butoxide in THF is added to the protected dephosphorylated FST intermediate (P—S) and reacted with Ps-3 to afford P—S2.

3. The two ethyl groups on the methoxyphosphate moiety of P—S2 are removed using bromotrimethylsilane in acetonitrile.

4. Deprotection of hydroxyl-protecting group can be achieved by any common methods known in the art, for example, by treating with HF-pyridine in HF—MeCN to afford the methoxyphosphorylated FST derivative B.

5. P—S2 compound may react with sodium bis(trimethylsilyl)amide in THF and fluorinating agent such as SELECT-FLUOR (manufactured by Air Products & Chemicals, Inc.) or solid N-fluoro benzenesulfonimide (NSFI), to afford α-fluorinated methoxyphosphorylated FST derivative intermediate.

6. The α-fluorinated methoxyphosphorylated FST derivative intermediate may proceed fluorination by treating with sodium bis(trimethylsilyl)amide and fluorinating agent, to afford the difluorinated methoxyphosphorylated FST derivative intermediate.

7. The deprotected compounds C and D can be obtained from α-fluoromethoxyphosphorylated FST derivative and difluorinated methoxyphosphorylated FST derivative intermediates, respectively by subjecting to step 3 and 4 above.

P—S2 may also be prepared from P—S according to the general method as shown in reaction scheme 2B.

The protected dephosphorylated FST intermediate is treated with polyoxymethylene in hydrochloric acid to afford the methyl chlorinated derivative, which then reacts with triethyl phosphate affords P—S2. Reaction of P—S2 compound with bromotrimethylsilane in DMF, followed by treating with NH₄OH affords the protected B-2 intermediate. B-2 compound can be obtained after deprotection.

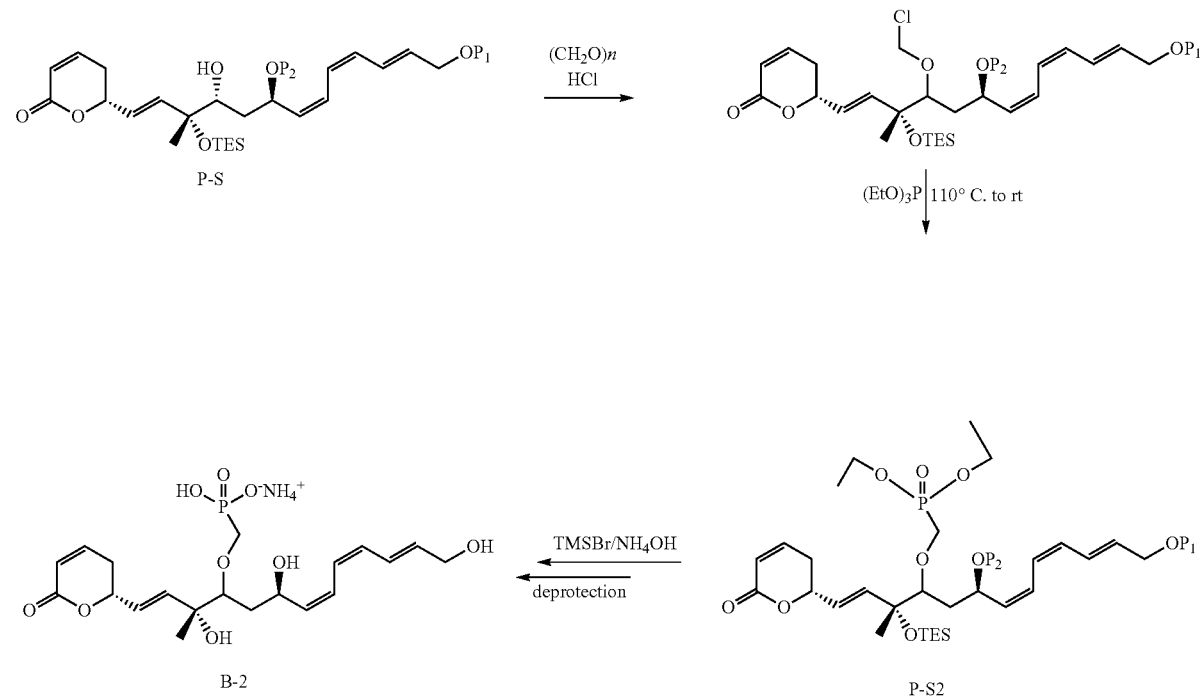

Compounds of formula I in some embodiments according to the present invention can be prepared using the general method for acylation as shown in the reaction scheme 3 below. For example, the particularly preferable compounds E and F can be prepared from dephosphorylated FST derivatives.

Reaction scheme 3:

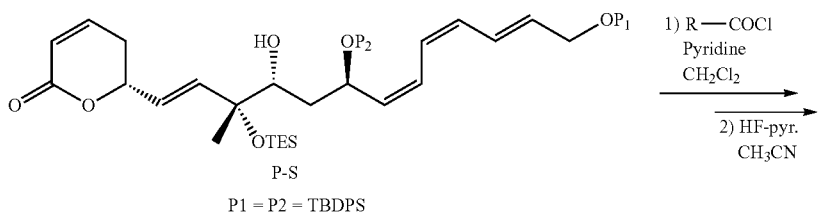

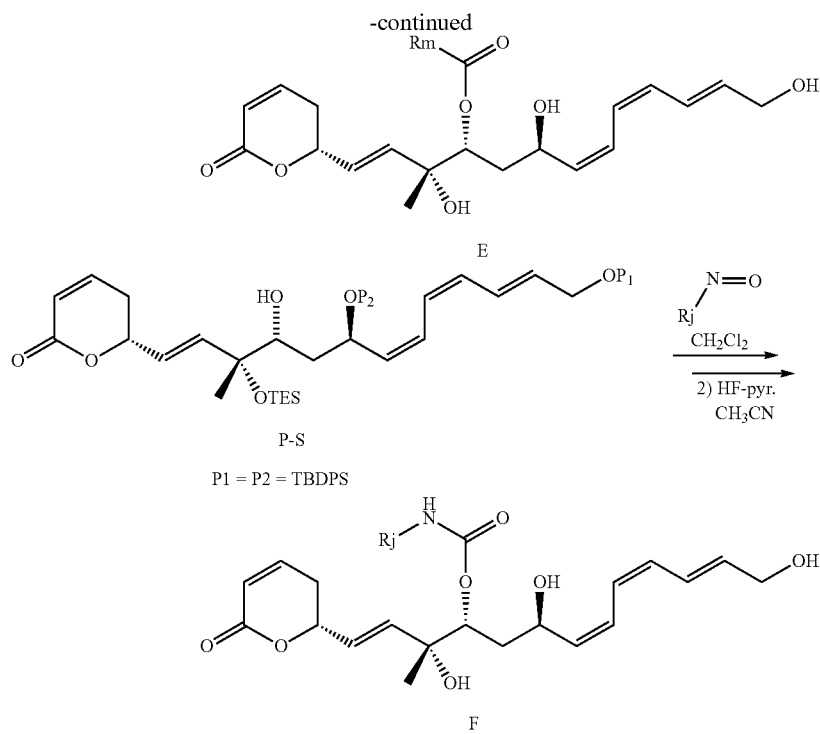

Reaction of P—S with acyl chloride in pyridine and dichloromethane affords the protected acylated FST derivative, deprotection is then achieved by treating with HF-pyridine in acetonitrile to afford compound E. Compound F, a more preferable compound from compound E, can be prepared by amidation of P—S.

The compounds of formula I in some embodiments according to the present invention, particularly a more preferable compound G, can be prepared from dephosphorylated FST derivative P-S using the general method as shown in the reaction scheme 4 below.

1. Allyl palladium π complex is formed by treating the protected FST derivative P—S with tetrakis(triphenyphosphine)palladium, followed by treating with sodium azide, and then subjecting to reduction using trimethylphosphine, to afford amino-FST derivative P—S3.

2. P—S3 and acid are subjected to amidation using the standard amide coupling agents such as diphenylphosphoryl azid/NaHCO₃ or EDC/HOBT (1-hydroxybenzotriazole) or bromo-tris-pyrrolidino-phosphonium hexafluorophosphate (PyBroP), to afford the protected intermediate.

Reaction scheme 4:

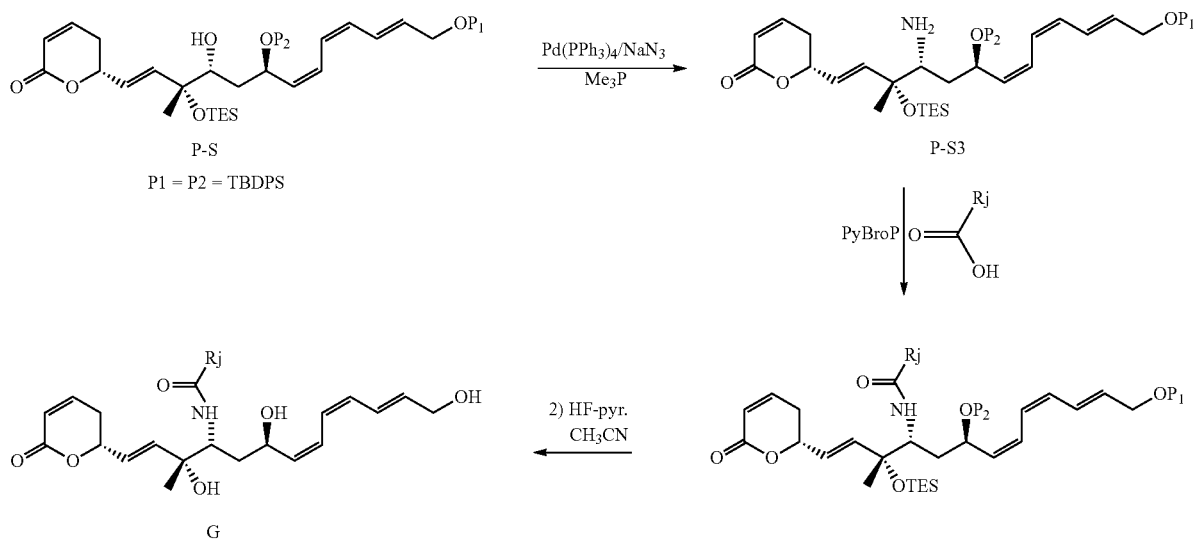

3. Deprotection by treating with HF-pyridine in acetonitrile affords compound G.

The compounds of formula I in some embodiments according to the present invention, preferablly compound H, can be prepared from amino-FST derivative P—S3 using the general method as shown in the reaction scheme 5 below.

(Rn in formula E, F, G and H above is defined as that for formula I, Rj is H, OH, an alkyl group or a halogen or NHRm, Rm is defined as H or a substituted lower alkyl group $C_{1-4}$ or an unsubstituted lower alkyl group $C_{1-4}$).

Reaction scheme 5:

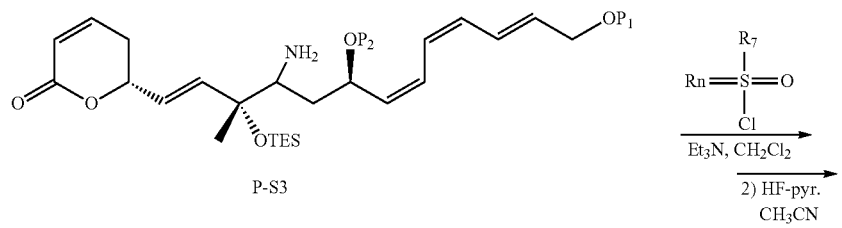

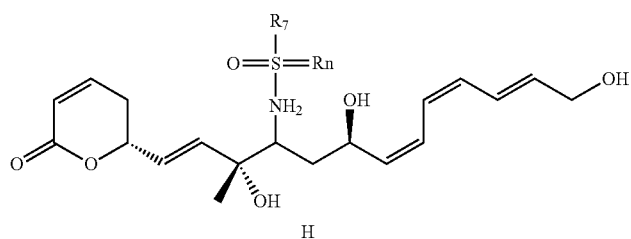

P—S3 is reacted with chloromethylated sulphate (or chlorophosphate) derivatives in Et3N (triethylamine) and dichloromethane to afford the protected methyl sulfonamide FST derivative H (wherein R7 is preferably methyl) or chlorophosphoric amide FST derivatives, followed by treating with HF-pyridine in acetonitrile to afford compound H.

Compound G or H can be prepared from dephosphorylated FST derivative P—S using the general method as shown in reaction scheme 6 below.

Reaction scheme 6:

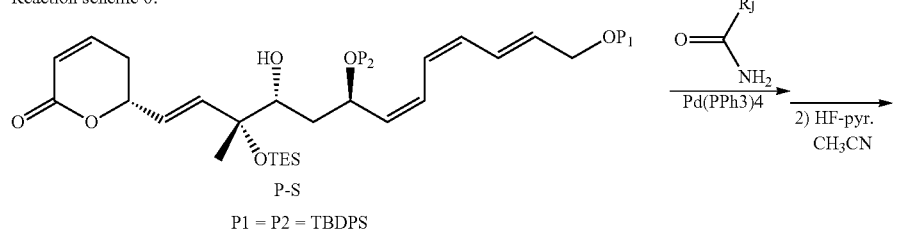

P1 = P2 = TBDPS

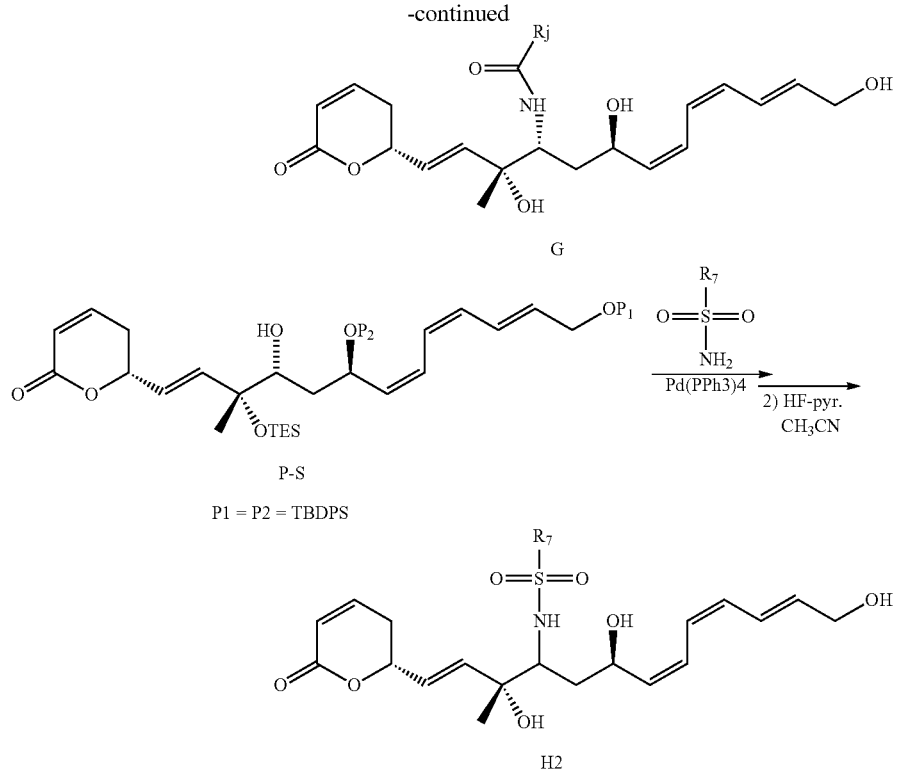

G

P-S
P1 = P2 = TBDPS

H2

Allyl palladium π complex is formed by treating the protected FST derivative P—S with tetrakis(triphenyphosphine) palladium, followed by treating with amine (such as amide or ammonium sulphate or ammonium phosphate) to afford the protected intermediate, and then treating with HF-pyridine in acetonitrile for deprotection to afford compound H2.

In some other embodiments, the present invention provides the compounds of formula (I) preferably having the following structure, which can be prepared by common methods known in the art and those described herein.

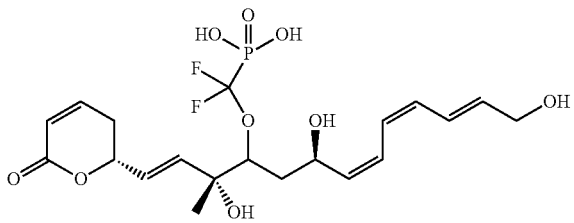

A

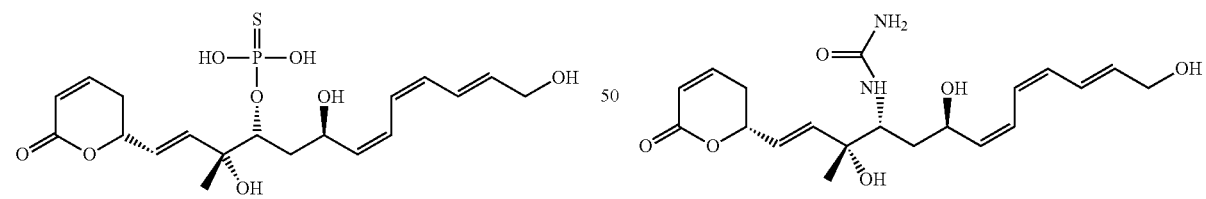

B

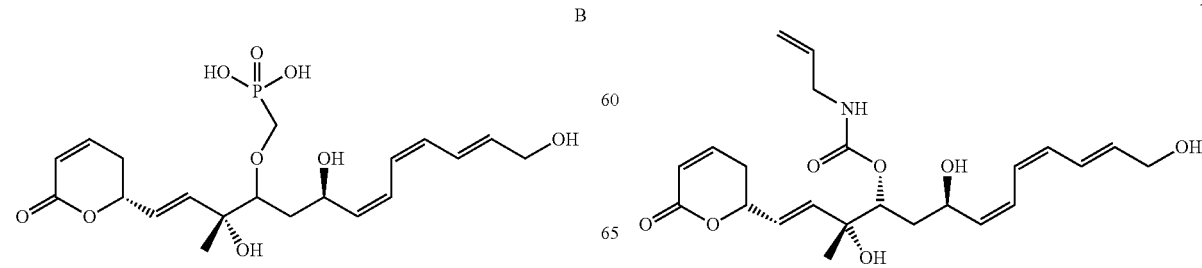

D

G

F

-continued

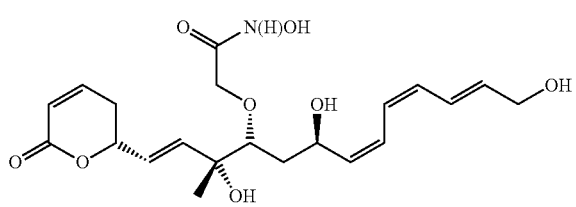

III-B3

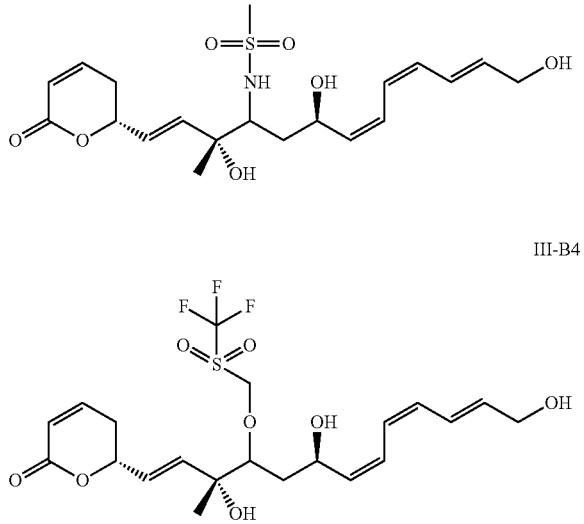

III-B4

The compounds of the present invention can be screened by conventional analytical methods known by one skilled in the art. For example, cytotoxicity of compounds and in vitro and in vivo stability of drugs can be determined. The present invention further provides the use of the FST derivatives of formula (I) in the preparation of the pharmaceutical compositions in treating tumors, inhibiting excessive growh of cell and terminating cell growth or lowering myocardial infarction and the injury to cells.

The compound of the present invention can be of free forms or derivatives thereof (for example, salts or esters thereof), conjugates or prodrugs thereof. Said compound may be in any states, such as solid, semi-solid or liquid. The compound of the present invention can be formulated with pharmaceutical acceptable carriers or diluents into a formulation for oral administration, intravenous administration or subcutaneous administration. Said pharmaceutical composition can be formulated according to standard methods employing solid or liquid carriers, diluents and additives suitable for the desired routes of administration. For oral administration, the compound of the present invention may be administered in the form of tablets, capsules, granules, and powders. The dosage range of the compound of the present invention is from about 0.05 to 200 mg/kg/day, which can be administered in a single dose or in multiple doses of 3 to 10 portions.

DETAILED DESCRIPTION OF THE INVENTION

Examples

Example 1

The Preparation of the Dephosphorylated FST By Hydrolysis of Alkaline Phosphatase

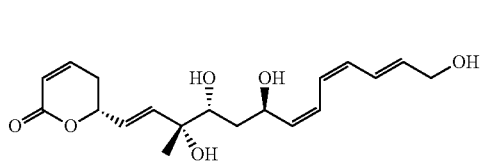

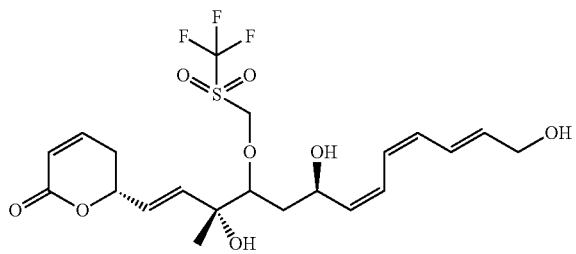

Reaction condidtions: FST was dissolved in a solution of 75 mM Tris Buffer (pH 8.3) and 5 mM $MgCl_2$ to obtain a 20 mM FST solution, to each milligram of Fostriecin was added 1 to 1.5 units of alkaline phosphatase, enzymolysis was performed at 37° C. for 2-5 hours.

MS(ESI+) of the thus obtained dephosphorylated FST ($C_{19}H_{26}O_6$): 351 $[M+H]^+$.

Figure 1:
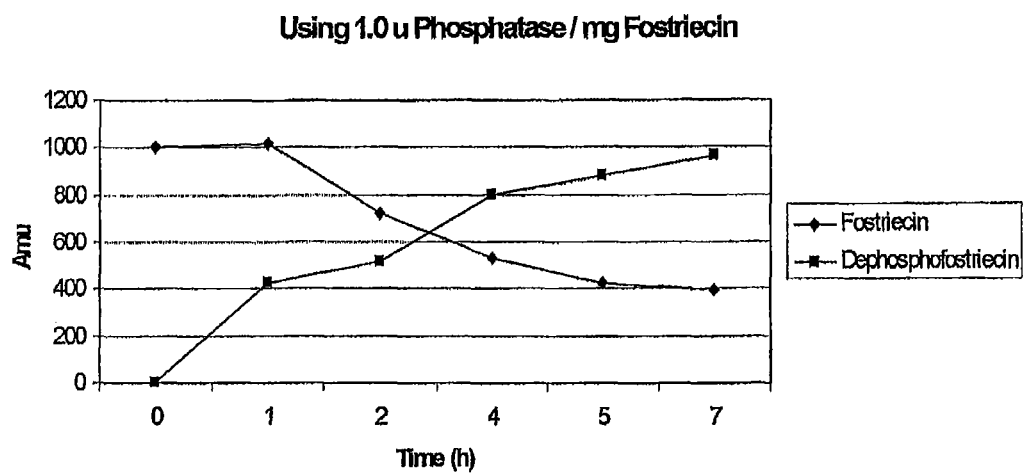
FIG. 1 shows the gradual formation of the dephosphorylated FST by enzymolysis of FST using alkaline phosphatase.

FIG. 1 shows the gradual formation of the dephosphorylated FST by enzymolysis of FST using alkaline phosphatase (dephosphofostriecin).

Example 2

Production of the Dephosphorylated FST By Genetic Recombination

The method of the present example employs the host strain capable of producing FST for genetic engeneering process. The FST biosynthetic genes and DNA sequences that can be used in the present invention is obtainable from natural resources, such as prepared from natural FST producing strains.

The DNA sequence (fosK gene) for encoding phosphorylated kinases (a homoserine kinases) in FST biosynthetic enzyme gene is inactivated by insertion of a neomycin resistance gene which results in the generation of the dephosphorylated FST, but no FST, by the FST producing strain. Subsequently, the engeineering strains were subjected to FST fermentation process that resembles that of its natural counterpart, the thus obtained ferment liquor was then separated by extraction to obtain the dephosphorylated FST compounds of the present invention.

Example 3

Preparation of the Thiophosphorylated FST

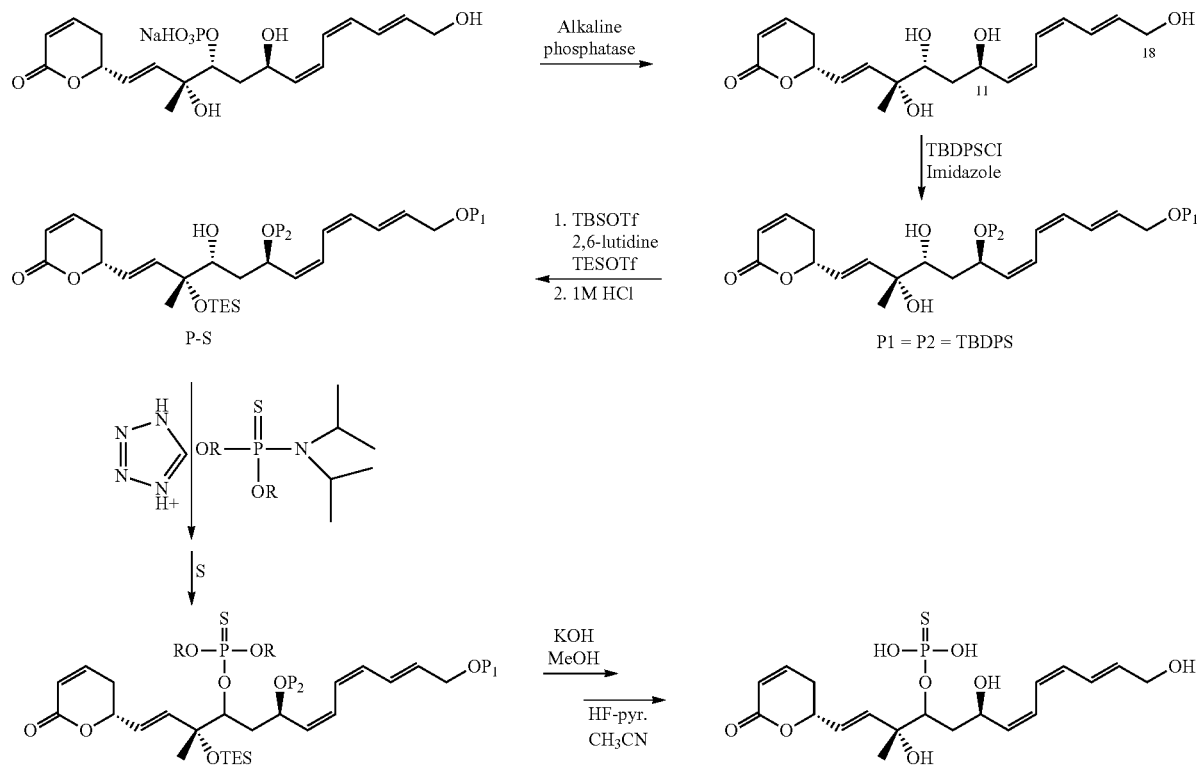

1. Dephosphorylated FST can be obtained by biochemical enzymolysis of FST as described in Example 1.

2. The thus obtained product from step 1 above was subjected to TBDPS protection (TBDPSCl, imidazole), which was then subjected to selective protection with TES (TBSOTf, 2,6-lutidine) according to the method as described by Boger et. al. (J. Am. Chem. Soc., 2001). Reaction was proceeded for 10 minutes at 25° C., and the mixture was evaporated to dry and subjected to SiO₂ chromatography for purification to afford the protected dephosphorylated FST intermediate (P—S). The protected dephosphorylated FST intermediate (12 mg) was dissolved in dichloromethane (3 ml), followed by addition of a solution of bis-(2-cyanoethyl)-N,N-diisopropylphosphoramidite (0.1 ml) and tetrazole (1M, 0.7 ml) in MeCN. The reaction mixture is then stirred at room temperature overnight, and followed by addition of 75 mg sulphur, and stirred at room temperature for 4 hours. The mixture is evaporated to dry and subjected to SiO₂ chromatography for purification to afford the protected thiophosphorylated FST intermediate.

3. The protected thiophosphorylated FST intermediate (4.9 mg) was dissolved in a 1N solution of KOH in methanol (2 ml), and stirred at room temperature for 2 hours, followed by deprotection of the hydroxyl-protecting group using common methods known in the art, for example, by treating with HF-pyridine in HF—MeCN to obtain the thiophosphorylated FST derivative A. Purification was achieved by reversed phase C18 chromatography. MS(ESI+) of the thiophosphorylated FST ($C_{19}H_{27}O_8PS$): 447 [M+H]$^+$

Example 4

Preparation of the Methyl Phosphorylated FST

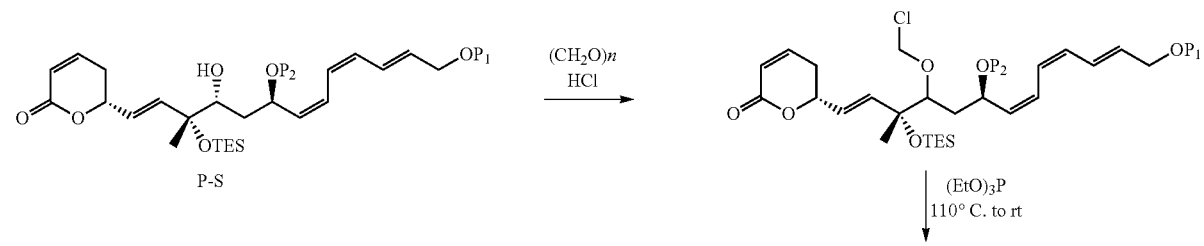

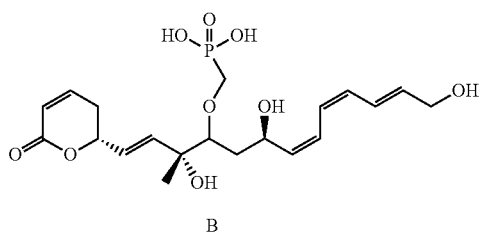

B

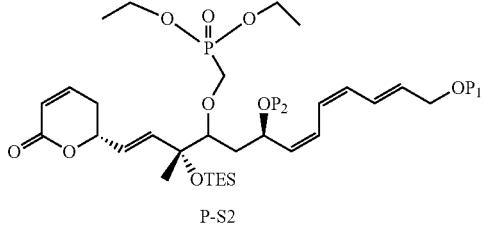

P-S2

1. To a solution of 0.22 mol P—S compound in 150 ml CH$_2$Cl$_2$ was added polyoxymethylene (0.23 mol). Gaseous hydrochloric acid was bubbled through the solution at 5° C. for 2 hours, which was then dried over MgSO$_4$ and filtered. The filtrate was subjected to evaporation to obtain the chlorinated FST intermediate.

2. The product (0.1 mol) obtained from step 1 above was heated together with triethyl phosphate to 110° C. Reaction was kept for 3 hours, and then subjected to vacuum drying, and purified by SiO$_2$ chromatography to obtain P—S2.

3. The protected dephosphorylated FST intermediate was then treated to afford the methyl chlorinated derivative which reacts with triethyl phosphate to afford P—S2 as well.

4. Bromotrimethylsilane (1.56 g) was added to a mixture of 1 g P—S2 and 0.9 g acetonitrile keeping the temperature below 50° C., and then washed with 0.3 g acetonitrile. The thus obtained mixture was refluxed at about 70° C. for 3 hours, and then dried under vacuum, purified by SiO$_2$ chromatography to afford the obtained product.

5. Deprotection of the hydroxyl-protecting group using common methods known in the art, for example by treating with HF-pyridine in HF—MeCN to afford the methyl phosphorylated FST derivative B. MS(ESI+) of the methyl phosphorylated FST(C$_{20}$H$_{29}$O$_9$P): 445 [M+H]$^+$.

Example 5

Figure 2:
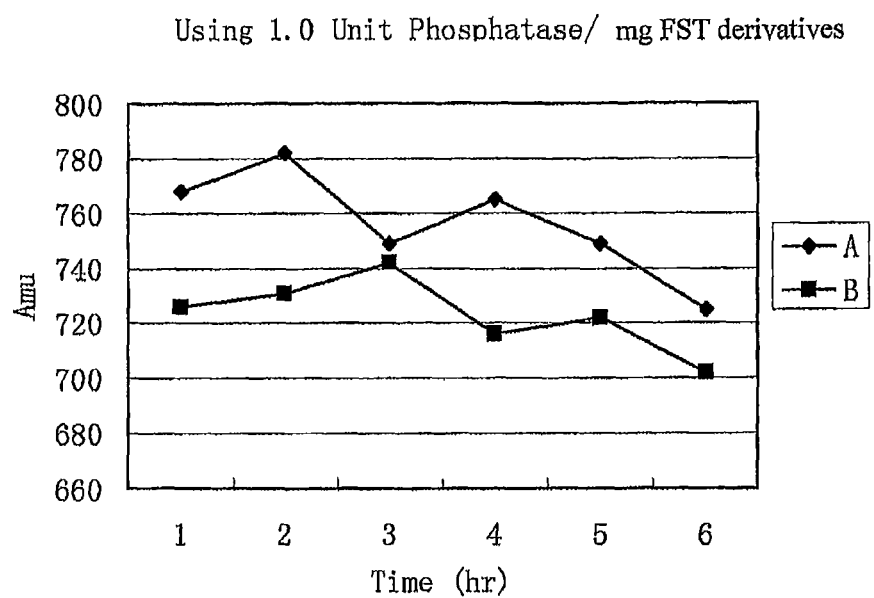
FIG. 2 shows the resistance of the FST derivative (thiophosphorylated FST (A) and methyl phosphorylated FST (B)) of the present invention to hydrolysis by alkaline phosphatase.

Resistance of Thiophosphorylated FST and Methyl Phosphorylated FST to Hydrolysis by Alkaline Phosphatase Thiophosphorylated FST(A) and methyl phosphorylated FST(B) were subjected to hydrolysis of alkaline phosphatase under the reaction condidtions as described in Example 1. FIG. 2 shows that thiophosphorylated FST and methyl phosphorylated FST were relatively stable under the action of alkaline phosphatase, and that no dephosphorylated FST was formed.

Example 6

Preparation of the Other FST Derivatives

Compound D (C$_{20}$H$_{27}$O$_9$PF2, MS(ESI+): 481 [M+H]$^+$) can be prepared from dephosphorylated FST derivative P—S using the general method as shown in reaction scheme 2; compound F (C$_{23}$H$_{31}$O$_7$N, MS(ESI+: 434 [M+H]$^+$) (i.e. compounds of formula E as Rm is allylamine or compounds of formula F as Rj is allyl) can be prepared from dephosphorylated FST derivative P—S using the general method as shown in reaction scheme 3; compound G (C$_{20}$H$_{28}$O$_6$N$_2$, MS(ESI+): 393 [M+H]$^+$) (i.e., compounds of formula G as Rj is NH$_2$) can be prepared from dephosphorylated FST derivative P—S using the general methods as shown in reaction scheme 4 or 6; compound H (C$_{20}$H$_{29}$O$_7$SN, MS(ESI+): 428 [M+H]$^+$) (i.e. compounds of formula H2 as Rn is O (oxygen), R7 is CH$_3$) can be prepared from dephosphorylated FST derivative P—S using the general method as shown in reaction scheme 5 or 6.

Example 7

In Vitro Anti-Tumor Activity of the Thiophosphorylated FST and Methyl Phosphorylated FST The anti-tumor activities of the compounds of thiophosphorylated FST (A) and methyl phosphorylated FST (B) of the present invention to various tumor cell lines of HL-60, CCRD-CEM and NCI-H460 were determined by Celltiter 96 cell proliferation assay kit (modified MTT method) manufactured by Promega company. Onto a 96-well plate, total volume 50 ul/well was added with about 5-7.5×10$^3$ cells/well, and cultured for 24 hours, followed by addition of 50 ul of the compounds (0.001 nM~1000 nM) to each well, and cultured for 72 hours. Subsequently, 15 ul of MTT staining solution was added to the well, temperature was kept for 4 hours, the thus formed precipitate was then dissolved with 100 ul lysis buffe/stop solution. After 1 hour, the content in the well was mixed homogeneously with a shaker, and the abosorption value (OD 570 nm) of each well was measured by enzyme-labeled instrument (Molecular Devices). The data was analyzed with Kaleida Graph Program, and the IC$_{50}$ value (the concentration of the compound at which the growth of 50% of the cell is inhibited) was calculated. The IC$_{50}$ of compound A, B and FST to the tumor cells are shown in the table below, wherein the unit for IC$_{50}$ value is μM.

TABLE 1

In vitro anti-tumor activity of the thiophosphorylated FST(A) and methyl phosphorylated FST(B) (IC$_{50}$; μM)

| | Tumor cells | | |
|---|---|---|---|
| compounds | HL60 (human leukemia) | CCRF-CEM (human leukemia) | NCI-H460 (human Lung Cancer) |
| FST | 12 | 10 | 14.5 |
| A | 10.5 | 9.6 | 13.2 |
| B | 12.5 | 14 | 16.3 |

What is claimed is:

1. A compound of the following formula (I):

formula I

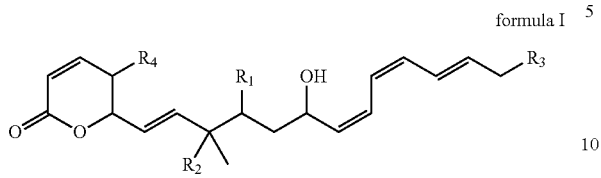

wherein, $R_1$ is

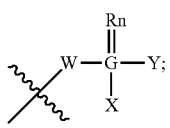

$R_1$ is not a phosphate group;

$R_2$, $R_3$ and $R_4$ are each independently selected from H, OH, $OR_5$, $NHR_6$ and a lower alkyl group;

W is O, O—CRjRj or NRj;

G is P, S or C;

X is $SR_6$, $OR_5$ or NHRj; as G is S, X=NRj or =O;

Y is $OR_5$, NHRj, $CF_3$, an unsubstituted lower alkyl group or a lower alkyl group substituted by a hydroxyl group, a lower acyloxy group, a lower alkanoyl group, a lower alkoxyl group, an amino group, a halogen, a lower alkylamido group or a lower amido group;

$R_5$ and $R_6$ are each independently H, Na, K, or an unsubstituted lower alkyl group or a lower alkyl group substituted by a hydroxyl group, a lower acyloxy group, a lower alkanoyl group, a lower alkoxyl group, an amino group, a halogen, a lower alkylamido group or a lower amido group;

As G is C, X does not exist;

Rn is O, NRj or S;

Rj is H, OH, an alkyl group or a halogen.

2. The compound according to claim 1, wherein $R_1$ is selected from the group consisting of:

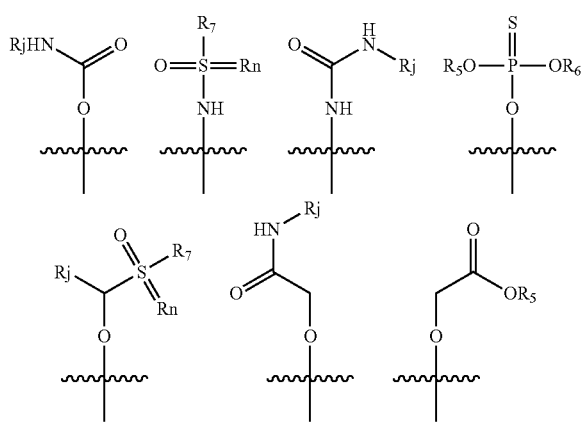

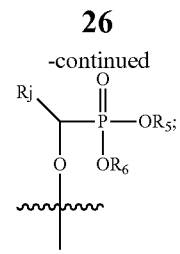

and wherein $R_7$ is methyl or $CF_3$.

3. The compound according to claim 1 having the following formula (III):

formula III

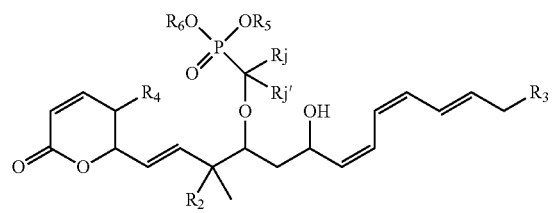

wherein Rj' is H, OH, an alkyl group or a halogen.

4. The compound according to claim 1, having one of the following formulas:

A

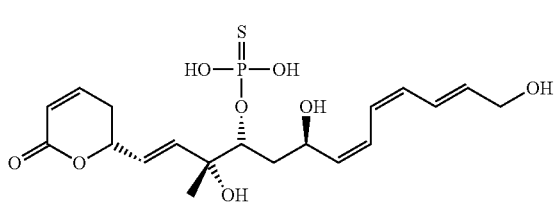

B

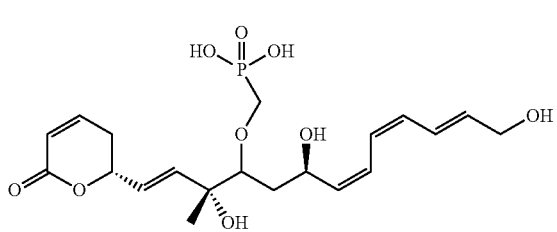

D

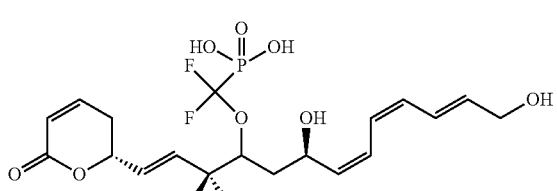

G

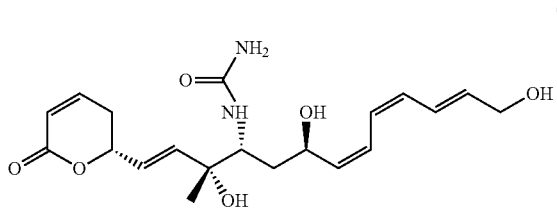

F

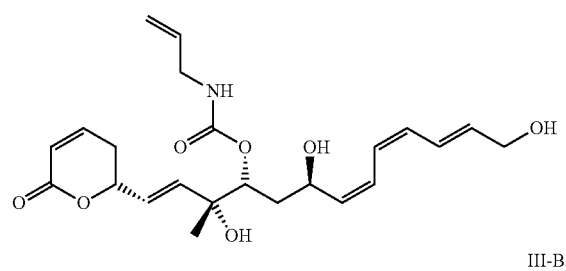

III-B3

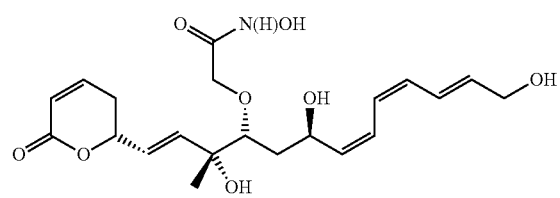

H

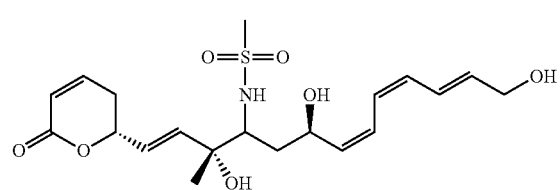

III-B4

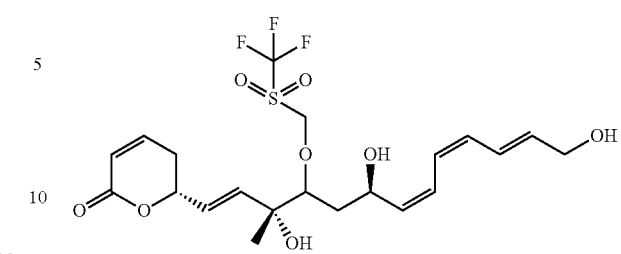

5. A pharmaceutical composition comprising the compound of claim 1 and a pharmaceutical acceptable carrier and/or diluent.

6. A pharmaceutical composition comprising the compound of claim 2 and a pharmaceutical acceptable carrier and/or diluent.

7. A pharmaceutical composition comprising the compound of claim 3 and a pharmaceutical acceptable carrier and/or diluent.

8. A pharmaceutical composition comprising the compound of claim 4 and a pharmaceutical acceptable carrier and/or diluent.

* * * * *